United States Patent [19]

Dexter

[11] Patent Number: 5,397,766
[45] Date of Patent: Mar. 14, 1995

[54] HERBICIDAL EMULSIFIABLE SUSPENSION CONCENTRATE COMPOSITIONS

[75] Inventor: Robin W. Dexter, Yardley, Pa.

[73] Assignee: American Cyanamid Company, Wayne, N.J.

[21] Appl. No.: 114,522

[22] Filed: Aug. 31, 1993

Related U.S. Application Data

[60] Division of Ser. No. 797,523, Nov. 25, 1991, Pat. No. 5,268,352, which is a continuation of Ser. No. 440,179, Nov. 22, 1989, abandoned.

[51] Int. Cl.$^6$ ........................... A01N 57/12
[52] U.S. Cl. ............................. 504/128; 504/127; 504/139; 71/DIG. 1
[58] Field of Search .............. 504/130, 139, 148, 128, 504/127

[56] References Cited

U.S. PATENT DOCUMENTS

| | | | |
|---|---|---|---|
| 3,799,758 | 3/1974 | Franz | 71/86 |
| 4,440,562 | 4/1984 | Prill | 71/86 |
| 4,798,619 | 1/1989 | Los | 71/92 |
| 4,816,060 | 3/1989 | Steller et al. | 71/92 |
| 4,835,026 | 8/1989 | Frisch et al. | 71/86 |

FOREIGN PATENT DOCUMENTS

| | | |
|---|---|---|
| 524025 | 4/1956 | Canada . |
| 0220902 | 5/1987 | European Pat. Off. . |
| 0243872 | 11/1987 | European Pat. Off. . |
| 2174395 | 11/1986 | United Kingdom . |
| WO8101787 | 7/1981 | WIPO . |
| WO8501286 | 3/1985 | WIPO . |

*Primary Examiner*—Peter O'Sullivan
*Assistant Examiner*—Brian M. Burn

[57] ABSTRACT

There are provided compositions comprising a concentrated amount of an herbicidally active agent, or combination of agents, in a solid state suspended in a water immiscible solvent containing an anionic surfactant and a nonionic surfactant and optionally containing an antifoam agent and a suspending or thickening agent. Upon dilution with hard or soft water, said compositions readily form sprayable herbicidal emulsions.

4 Claims, No Drawings

HERBICIDAL EMULSIFIABLE SUSPENSION CONCENTRATE COMPOSITIONS

This is a divisional of application Ser. No. 07/797,523, filed on Nov. 25, 1991, now U.S. Pat. No. 5,268,352, which is a continuation of application Ser. No. 07/440,179, filed on Nov. 22, 1989, abandoned.

BACKGROUND OF THE INVENTION

This invention relates to novel and useful agricultural formulations of herbicidal agents which exhibit poor solubility characteristics in both aqueous and organic media.

Emulsifiable suspension concentrate compositions (or oil flowable dispersions) are compositions which consist essentially of an active agent in a solid state suspended in a non-aqueous liquid containing a surfactant or a mixture of surfactants and said compositions having the property of forming an emulsion when diluted with water.

Emulsifiable suspension concentrate compositions containing pesticides such as herbicides and fungicides as the active agent and paraffinic oils as the non-aqueous liquid are described in European Patent Applications EP-A1-243872 and EP-A2-142670. However, said patent applications do not describe the use of aromatic solvents as the non-aqueous liquid.

Herbicidal agents, such as N-phosphonomethylglycine (glyphosate) and 2-(4-isopropyl-4-methyl-5-oxo-2-imidazolin-2-yl)nicotinic acid (imazapyr), are especially useful for controlling undesirable plant species when applied postemergence. In addition to being highly effective herbicides, said compounds are zwitterionic in nature and generally relatively insoluble in both aqueous and non-aqueous media. Therefore, these types of herbicidal agents are routinely formulated as the corresponding salts as described in European Patent Application EP-A2-220902 and U.S. Pat. No. 4,816,060.

It is an object of this invention to provide an emulsifiable suspension concentrate composition of the free acids of a herbicidal agent, such as N-phosphonomethylglycine and 2-(imidazolin-2-yl)pyridine carboxylic acids, without the pre-formulation of the corresponding herbicidal salts. It is an object of this invention to produce herbicidal compositions which are physically stable and readily dilutable in hard or soft water to give a sprayable herbicidal emulsion.

SUMMARY OF THE INVENTION

The present invention relates to a novel emulsifiable suspension concentrate composition of a herbicidal agent characterized by a relative degree of insolubility in both aqueous and non-aqueous media. The emulsifiable suspension concentrate composition of the invention is comprised of an active herbicidal agent, or combination of agents, in a solid state suspended in a water immiscible solvent containing an anionic surfactant and a nonionic surfactant and optionally containing an antifoam agent and a suspending or thickening agent.

The water immiscible solvent is a non-paraffinic heavy aromatic solvent consisting of a mixture of aromatic hydrocarbons, such as naphthalenes and alkylnapthalenes, having a distillation range of about 118° to 305° C.

The above-described compositions allow the formulation of active herbicidal agents such as amino acids and imidazolinylnicotinic acids without further chemical modifications, such as salt or ester formation. The above compositions provide a stable, concentrated, readily dilutable form of a herbicide suitable for spray application. The compositions also exhibit surprising herbicidal efficacy comparable to the efficacy of the corresponding salts.

DETAILED DESCRIPTION OF THE INVENTION

The present invention also relates to an emulsifiable suspension concentrate composition of a herbicidal agent comprising an amino acid or imidazolinylpyridine carboxylic acid (alone or in combination) in a solid state suspended in a water immiscible liquid containing an anionic surfactant and an ethoxylated fatty acid surfactant and optionally containing an antifoam agent and a thickening or suspending agent.

The herbicidal agent is usually sold in a concentrated form either as a solid or a liquid and, just prior to application, the concentrate is diluted with water, or water containing adjuvants, and sprayed on fields of soil and/or actively growing plants. Solid concentrate formulations, such as granulars, wettable powders and dusts, may also be used.

Since not all solid concentrate formulations of the free acid form of herbicidal agents, such as N-phosphonomethylglycine, exhibit the same high magnitude of efficacy and further since certain highly effective herbicidal compounds, such as N-phosphonomethylglycine and imidazolinylnicotinic acids, are relatively insoluble in water and conventional organic solvents, they are not readily amenable to commercial formulation. Chemical modification of said compounds to give the corresponding salts is required to improve their solubility characteristics. Surprisingly, it has been found that compounds, such as amino acids and imidazolinylnicotinic acids, may be formulated as liquid concentrates without further chemical modifications of said compounds and with a high degree of retention of efficacy.

The emulsifiable suspension concentrate compositions of the present invention are comprised of about 10% to 50% of a herbicidal agent, such as N-phosphonomethylglycine or an imidazolinylnicotinic acid, alone or in combination, suspended in about 29% to 84% of a non-paraffinic aromatic solvent mixture having a distillation range of 118° to 305° C. containing about 3% to 10% of an anionic surfactant, about 3% to 10% of an ethoxylated fatty acid surfactant, 0 to about 0.10% of an antifoam agent and 0 to about 2.0% of a suspending or thickening agent.

One preferred composition comprises about 30% to 50% of an active herbicidal agent or combination of agents, about 40% to 57% of a non-paraffinic aromatic solvent mixture having a distillation range of 118° to 305° C., about 5.0% to 7.0% of an anionic surfacant, about 5.0% to 7.0% of an ethoxylated fatty acid surfactant, about 0.02% to 0.15% of an antifoam agent and 0.5 to 2% of a suspending agent.

Among the herbicidal agents suitable for use in the compositions of the invention are amino acids such as glyphosate and imidazolinylpyridine carboxylic acids such as imazapyr and combinations thereof. A preferred herbicidal agent is glyphosate, alone or in combination with an imidazolinylnicotinic acid.

Solvents suitable for use in the compositions of the invention include heavy aromatic solvent mixtures having a distillation range of 118° to 305° C. Preferred solvents include those mixtures of aromatics having a distillation range of about 183° to 285° C., and the most preferred aromatic solvent mixtures is that which distills in a range of about 225° to 280° C. Anionic surfactants suitable for use in the present invention include alkylarylsulfonic acids such as $C_8$-$C_{18}$ alkylbenzenesulfonic acid, with dodecylbenzenesulfonic acid being the preferred anionic surfactant.

Among the ethoxylated fatty acid surfactants which may be employed are ethoxylated castor oils with about 15-60 ethylene oxide units per molecule. Preferred ethoxylated castor oils are those which have about 36-40 ethylene oxide units per molecule. Suitable antifoam agents include silicone polymers containing silica such as dimethylsilicone polymer plus silica, and suitable suspending or thickening agents include hydrated fumed silica or attapulgite clays or amine treated attapulgite clays.

The herbicidal emulsifiable suspension concentrate compositions may be prepared by dissolving an anionic surfactant in an aromatic solvent and adding a solid herbicidal agent or combination of agents, with vigorous agitation to form a suspension. This suspension is milled to the required particle size distribution. A median particle diameter of 1-2 microns provides suitable physical properties. The milled suspension is treated with an ethoxylated fatty acid surfactant and, optionally, an antifoam agent and a suspending or thickening agent and mixed thoroughly. Alternatively, the herbicidal agent is milled as a dry powder and is added to a solution of the anionic surfactant in the aromatic solvent with vigorous agitation to ensure complete dispersion and the remaining components are added with stirring.

The above-prepared emulsifiable suspension concentrate compositions are physically stable and demonstrate excellent dilution properties in hard and soft waters to produce a sprayable herbicidal emulsion. In practice, it is generally preferable to dilute the compositions of the invention in water containing about 0.25% of an adjuvant such as a polyoxyethylene sorbitan laurate surfactant to obtain an especially high degree of herbicidal activity.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

| Component | % |
|---|---|
| N-phosphonomethylglycine | 41.90 |
| Dodecylbenzenesulfonic acid | 6.00 |
| Ethoxylated castor oil, 36 C.[1] | 6.00 |
| Dimethylsilicone polymer with silica[2] | 0.10 |
| Mixture of aromatic hydrocarbons with a distillation range of 226°-279° C.[3] | 46.00 |
| | 100.00 |

[1]36 units of ethylene oxide per molecule Flomo ® 36 C., manufactured by DeSoto
[2]TH 100IND ® antifoam, manufactured by Thompson-Hayward
[3]Aromatic 200°, manufactured by EXXON Method 1

An anionic surfactant, dodecylbenzenesulfonic acid, is dissolved in a water immiscible solvent, Aromatic 200 ®, with stirring. This solution is treated with the herbicidal agent, N-phosphonomethylglycine, in a crystalline or powder state with vigorous stirring to give a dispersion. The resultant dispersion is milled until a median particle size of 1-2 microns is obtained.

The milled dispersion is treated with an ethoxylated fatty acid surfactant, castor oil, 36C[1], and an antifoam agent, dimethylsilicone polymer with silica[2] and mixed thoroughly.

Method 2

The herbicidal agent, N-phosphonomethylglycine, is milled to give a median particle size of 1-2 microns and then added to a solution of an anionic surfactant, dodecylbenzenesulfonic acid in a water immiscible solvent, Aromatic 200 ®, with vigorous agitation. The resultant dispersion is treated with an ethoxylated fatty acid surfactant, castor oil, 36C[1], and an antifoam agent, dimethylsilicone polymer plus silica[2], and mixed thoroughly.

Physical Properties

The physical characteristics of the above-described N-phosphonomethylglycine emulsifiable concentrate composition are shown below.

| | |
|---|---|
| Viscosity (Brookfield LVT at 22° C. spindle #2, speed 30 rpm) | 500-600 cP |
| Density at 20° C. | 1.41 g/mL |
| Particle size (Horiba CAPA 700) | 1.21 microns (median) |
| pH, 2% diluted in deionized water | 2.0-2.4 |
| Dispersibility in water (in both standard hard and soft waters), 2.5 g in 100 ml total volume. | Good emulsification, no oil separation after 24 hours. |

EXAMPLE 2

| Components | A | B |
|---|---|---|
| Imazethapyr | — | 33.3 |
| Imazapyr | 33.33 | — |
| Dodecylbenzenesulfonic acid | 5.00 | 5.00 |
| Ethoxylated castor oil, 36 C.[1] | 5.00 | 5.00 |
| Dimethylsilicone polymer with silica[2] | 0.03 | 0.03 |
| Mixture of aromatic hydrocarbons with a distillation range of 226°-279° C. | 56.64 | 56.64 |
| | 100.00 | 100.00 |

[1]36 units of ethylene oxide per molecule Flomo ® 36 C., manufactured by DeSoto
[2]TH IND30 ® antifoam, manufactured by Thompson-Hayward
[3]Aromatic 200 ®, manufactured by EXXON Method The herbicidal agent, as a finely divided powder, is added to a rapidly stirred solution of the anionic surfactant, dodecylbenzenesulfonic acid, in the aromatic solvent, Aromatic 200 ®. The resultant dispersion is treated with the remaining components and placed on a high shear mixer for 3 minutes.

Optionally the solid herbicidal agent is milled to a median particle size of 1-2 microns prior to use in the above-described preparation.

| Physical Properties | A | B |
|---|---|---|
| Dispersibility in water, 4.0 g in 100 ml total volume. | Good emulsification, slight settling after 24 hours, easily resuspended | Good emulsification, slight settling after 24 hours, easily resuspended |

EXAMPLE 3

| Preparation of combination emulsifiable suspension concentrate compositions | | |
|---|---|---|
| Components | C | D |
| Glyphosate | 37.69 | 32.89 |
| Imazapyr | 4.20 | 9.00 |
| Dodecylbenezenesulfonic acid | 6.00 | 6.00 |
| Flomo ® 36 C.[1] | 6.00 | 6.00 |
| TH 100IND ® antifoam[1] | 0.10 | 0.10 |
| Aromatic 200 ®[1] | 46.01 | 46.01 |
|  | 100.00 | 100.00 |

[1]As described in Example 1.

Method

A solution of dodecylbenzene in Aromatic 200 ® is treated with glyphosate with rapid stirring. The resultant dispersion is treated with the remaining components and placed on a high shear mixer for 3 minutes.

Optionally, a dispersion of glyphosate and the imidazolinylnicotinic acid solid in a solution of dodecylbenzenesulfonic acid in Aromatic 200 ® is milled to give a median particle size of 1–2 microns prior to the addition of the remaining components.

| Physical Properties | C | D |
|---|---|---|
| Dispersibility in water, 4.0 g in 100 ml total volume. | Good emulsification, slight oil separation after 24 hours, easily resuspended | Good emulsification, slight oil separation after 24 hours, easily resuspended |

EXAMPLE 4

Greenhouse Postemergent Herbicidal Evaluation

This is an evaluation of the postemergent herbicidal activity of the emulsifiable suspension concentrate composition of N-phosphonomethylglycine as compared to a commercial aqueous solution composition of the isopropylammonium salt of N-phosphonomethylglycine.

The test compositions used for this evaluation are the emulsifiable suspension concentrate composition of N-phosphonomethylglycine which is described in Example 1 and referred to herein as Glyphosate 40 ESC and an aqueous soluble composition of the isopropylammonium salt of N-phosphonomethylglycine which is commercially sold by Monsanto under the trademark ROUNDUP ® and referred to herein as Glyphosate Salt.

Seedling plants are grown in jiffy flats for about 2 weeks. The glyphosate 40 ESC composition is dispersed in water containing 0.25% TWEEN-20 ®, a polyoxyethylene sorbitan monolaurate surfactant manufactured by Atlas Chemical Industries in sufficient quantity to provide the equivalent of about 0.063 kg to 0.500 kg per hectare of N-phosphonomethylglycine to the plants when applied through a spray nozzle operating at 40 psi for a predetermined time. The Glysphosate Salt is dispersed in water according to the label directions and applied to the plants as described above. After spraying, the plants are placed on greenhouse benches and cared for in the usual manner commensurate with conventional greenhouse practices. The plants are evaluated at 7 and 14 days after treatment and rated according to the rating system shown below.

| Rating System | % Control |
|---|---|
| No effect | 0 |
| Possible effect | 1–10 |
| Slight effect | 11–25 |
| Moderate effect | 26–40 |
| Definite injury | 41–60 |
| Herbicidal effect | 61–75 |
| Good Herbicidal effect | 76–90 |
| Approaching complete kill | 91–99 |
| Complete kill | 100 |

| Plant Species Used | |
|---|---|
| Common Name | Scientific Name |
| Mustard Wild | Brassica kaber |
| Cotton | Gossypium hirsustum |
| Corn | Zea mays |
| Morningglory | Ipomoea purpurea |
| Soybean | Glycine max |
| Barnyard Grass | Echinochloa crus-galli |
| Lambsquaters | Chenopidium album |
| Ragweed | Ambrosia artemisifolia |
| Green Foxtail | Setaria veridis |

The data obtained at 14 days after treatment are reported in Table I below.

TABLE I

| | Postemergence Herbicidal Evaluation | | | | | | | | | |
|---|---|---|---|---|---|---|---|---|---|---|
| Composition | Rate (ka/ha) | Must ard | Cot ton | Field Corn | Morn glry | Soy bean | Barn yardg | Lambs quart | Rag weed | Grn Fox tail |
| Glyphosate Salt | 0.500 | 80.0 | 80.0 | 90.0 | 66.7 | 78.3 | 98.7 | 99.3 | 38.3 | 100.0 |
| Glyphosate ESC | 0.500 | 60.0 | 50.0 | 95.0 | 71.7 | 80.0 | 94.3 | 96.3 | 40.0 | 91.7 |
| Glyphosate Salt | 0.250 | 38.3 | 35.0 | 58.3 | 63.3 | 63.3 | 71.0 | 83.3 | 33.3 | 85.0 |
| Glyphosate ESC | 0.250 | 33.3 | 40.0 | 85.3 | 75.3 | 71.7 | 78.3 | 100.0 | 53.3 | 93.3 |
| Glyphosate Salt | 0.125 | 13.3 | 20.0 | 18.3 | 30.0 | 20.0 | 23.3 | 61.7 | 6.7 | 46.7 |
| Glyphosate ESC | 0.125 | 26.7 | 3.3 | 71.7 | 30.0 | 50.0 | 48.3 | 83.3 | 23.3 | 81.7 |
| Glyphosate Salt | 0.063 | 0.0 | 3.3 | 3.3 | 15.0 | 6.7 | 16.7 | 36.7 | 0.0 | 20.0 |
| Glyphosate ESC | 0.063 | 6.7 | 0.0 | 61.7 | 10.0 | 20.0 | 35.0 | 70.0 | 13.3 | 40.0 |

EXAMPLE 5

Field Postemergent Herbicidal Evaluation

The test compositions used are Glyphosate 40 ESC and Glyphosate Salt, and are as described in Example 4.

A field containing established, actively growing plants is divided into plots of 10 meters × 30 meters and is sprayed with a tractor mounted compressed air sprayer with a delivery of 200 liters per hectare. The Glyphosate 40 ESC composition is dispersed in water containing 0.25% TWEEN-20 ® in sufficient quantity to provide the equivalent of 2.0 kg to 0.5 kg per hectare to the plants. Glyphosate Salt is dispersed in water according to the label directions and applied to the plants as described hereinabove. The plots are evaluated at 7 and 14 days after treatment. Each treatment is replicated once. The data obtained for 14 days after treatment is reported in Table II.

| Plant Species | |
|---|---|
| Common Name | Scientific Name |
| Redroot pigweed | Amoranthus retroflexus |
| Common lambsquarters | Chenopodium album |
| Common purslore | Portulara oleracea |
| Common ragweed | Ambrosia artemisiifola |
| Large crabgrass | Digitaria sanguiralis |
| Fall panicum | Panicum diclotomiflorum |
| Barnyard grass | Echirochloa curs-galli |
| Foxtail millet | Setaria italica |

TABLE II

| | | Postemergence Field Evaluation | | | | | | |
|---|---|---|---|---|---|---|---|---|
| Composition | Rate kg/ha | Red Root Pig weed | Lambs quart | Rag weed | Crab gras | Fall pani | Bard yardq | Fox tail millet |
| Glyphosate Salt | 0.5 | 100 | 80 | 98 | 100 | 95 | 100 | 100 |
| Glyphosate ESC | 0.5 | 100 | 100 | 85 | 100 | 98 | 100 | 100 |
| Glyphosate Salt | 1.0 | 100 | 100 | 100 | 100 | 100 | 100 | 100 |
| Glyphosate ESC | 1.0 | 100 | 100 | 100 | 100 | 100 | 100 | 100 |
| Glyphosate Salt | 2.0 | 100 | 100 | 100 | 100 | 100 | 100 | 100 |
| Glyphosate ESC | 2.0 | 100 | 100 | 100 | 100 | 100 | 100 | 100 |

I claim:

1. A suspension concentrate composition of a herbicidal agent which comprises a herbicidal agent, an aromatic hydrocarbon mixture having a distillation range of about 118° C. to 305° C., a $C_8$–$C_{18}$ alkylbenzenesulfonic acid, an ethoxylated castor oil with about 15–60 ethylene oxide units per molecule and optionally an antifoam agent and a suspending agent, wherein the herbicidal agent is a 2-(imidazolin-2-yl) pyridine carboxylic acid derivative or N-phosphonomethylglycine in combination with a 2(imidazolin-2-yl) pyridine carboxylic acid derivative.

2. The composition according to claim 1 wherein the herbicidal agent is selected from the group consisting of 2-(4-isopropyl-4-methyl-5-oxo-2-imidazolin-2-yl)nicotinic acid, 5-ethyl-2-(4-isopropyl-4-methyl-5-oxo-2-imidazolin-2-yl)nicotinic acid and 5-methyl-2-(4-isopropyl-4-methyl-5-oxo-2-imidazolin-2-yl)nicotinic acid.

3. The composition according to claim 2 comprising about 30.0% to 50.0% of the herbicidal agent, about 40.0% to 60.0% of the aromatic hydrocarbon mixture having a distillation range of about 183° C. to 285° C., about 4.0% to 8.0% of the $C_8$–$C_{18}$ alkylbenzenesulfonic acid, about 4.0% to 8.0% of the ethoxylated castor oil and 0 to about 2.0% of the antifoam agent.

4. The composition according to claim 1 comprising about 30.0% to 40.0% of N-phosphonomethylglycine in combination with about 0.5% to 10.0% of the 2-(imidazolin-2-yl) pyridine carboxylic acid derivative, about 45.0% to 60.0% of the aromatic hydrocarbon mixture having a distillation range of about 183° C. to 285° C., about 4.0% to 8.0% of the $C_8$–$C_{18}$ alkylbenzenesulfonic acid, about 4.0% to 8.0% of the ethoxylated castor oil and 0 to about 2.0% of the antifoam agent.

* * * * *